United States Patent [19]

Hamilton et al.

[11] Patent Number: 5,449,835
[45] Date of Patent: Sep. 12, 1995

[54] SYNTHESIS OF BIS(2,2-DINITHROPROPYL) FORMAL (BDNPF)

[75] Inventors: R. Scott Hamilton, Bear River City; Robert B. Wardle, Logan, both of Utah

[73] Assignee: Thiokol Corporation, Ogden, Utah

[21] Appl. No.: 339,140

[22] Filed: Nov. 14, 1994

[51] Int. Cl.6 ............... C07C 41/50; C07C 43/30
[52] U.S. Cl. .................................. 568/590; 149/88
[58] Field of Search .................................. 568/590

[56] References Cited

U.S. PATENT DOCUMENTS

| | | |
|---|---|---|
| 1,312,186 | 8/1919 | King et al. |
| 2,227,128 | 12/1940 | Ellis ............................. 568/590 |
| 2,388,409 | 11/1945 | Harvey ......................... 260/615 |
| 2,415,046 | 1/1947 | Senkus ......................... 260/611 |
| 2,519,540 | 8/1950 | Bramyche et al. ............ 260/615 |
| 2,535,458 | 12/1950 | Robeson ....................... 260/615 |
| 2,875,252 | 2/1959 | Elam et al. ................... 260/615 |
| 3,288,863 | 11/1966 | Hall et al. .................... 260/615 |
| 3,291,833 | 12/1966 | Gold et al. ................... 260/584 |
| 3,523,808 | 8/1970 | Gold et al. ................... 106/287 |
| 3,526,667 | 9/1970 | Hill et al. ..................... 260/615 |
| 3,629,338 | 12/1971 | Martin ......................... 260/615 A |
| 4,048,219 | 9/1977 | Adolph ......................... 560/156 |
| 4,062,897 | 12/1977 | Adolph ......................... 260/615 A |
| 4,374,241 | 2/1983 | Adolph ......................... 528/266 |
| 4,453,021 | 6/1984 | Adolph ......................... 568/590 |
| 4,756,777 | 7/1988 | Koppes et al. ................ 149/88 |
| 4,841,075 | 6/1989 | Matsushita et al. .......... 549/341 |
| 4,997,499 | 3/1991 | Adoph .......................... 149/88 |

Primary Examiner—Joseph E. Evans
Attorney, Agent, or Firm—Lyons: Ronald L.; Madson & Metcalf

[57] ABSTRACT

A nonsolvent process of synthesizing bis(2,2-dinitropropyl)formal (BDNPF) is disclosed. In the process, 2,2-dinitropropanol (DNPOH) is reacted at low temperature with a formaldehyde source in the presence of a protic acid catalyst, such as $H_2SO_4$, HCl, $H_3PO_4$, or HBr. To inhibit byproduct formation, the reaction temperature is maintained from about $-30°$ C. to $30°$ C. Upon completion of the reaction, the reaction solution is quenched with water and washed with an aqueous hydroxide ion solution. The hydroxide ion concentration should be sufficient to neutralize the protic acid catalyst during the quenching step and to solubilize unreacted 2,2-dinitropropanol as well as other aqueous soluble byproducts in the reaction solution. The BDNPF product is extracted with a low boiling temperature polar organic solvent, such as methyl tert-butyl ether (MTBE) or equivalent solvent. The organic solvent is evaporated to yield usable BDNPF product. The resulting yield is at least 60% based on the starting quantity of 2,2-dinitropropanol.

15 Claims, No Drawings

SYNTHESIS OF BIS(2,2-DINITHROPROPYL) FORMAL (BDNPF)

GOVERNMENT RIGHTS

The United States Government has a paid-up license in this invention and the right in limited circumstances to require the patent owner to license others on reasonable terms as provided for by the terms of contract No. DAAA21-94-D-0003 awarded by the U.S. Army.

FIELD OF THE INVENTION

The present invention relates to synthesis of bis(2,2-dinitropropyl)formal (BDNPF) without the use of a solvent medium.

BACKGROUND OF INVENTION

Bis(2,2-dinitropropyl)formal (BDNPF) is an energetic plasticizer used in propellant and explosive applications. Because BDNPF is a solid at room temperature, BDNPF is usually combined with liquid bis(2,2-dinitropropyl)acetal (BDNPA) in a 50:50 weight percent mixture. The mixture of BDNPF and BDNPA is a liquid. BDNPA/BDNPF is a commercialized product.

The current method for synthesizing BDNPF requires a methylene chloride solvent system. However, there is growing environmental concern about chlorinated solvents' potential contribution to ozone depletion and possible carcinogenic properties. Thus, it would be a significant advancement in the art to provide a method for synthesizing BDNPF which does not use chlorinated solvents.

In addition, the use of a solvent in a chemical manufacturing process adds the need for solvent separation and waste disposal procedures. For instance, it is believed the current BDNPF manufacturing process has a high temperature (about 125° C.) vacuum evaporation step to remove the methylene chloride solvent and minor volatile byproduct impurities. Such evaporation not only increases manufacturing costs, but also represents a safety hazard by subjecting energetic materials to high temperatures.

It will be appreciated that there is a need in the art for a process of synthesizing BDNPF which does not require the use of chlorinated solvents, and which avoids costly and dangerous evaporation procedures.

Such methods of synthesizing BDNPF are disclosed and claimed herein.

SUMMARY OF THE INVENTION

The present invention is directed to a process of synthesizing bis(2,2-dinitropropyl)formal (BDNPF). In the process, 2,2-dinitropropanol (DNPOH) is reacted at low temperature with a formaldehyde source in the presence a protic acid catalyst, such as $H_2SO_4$. The reaction is shown below:

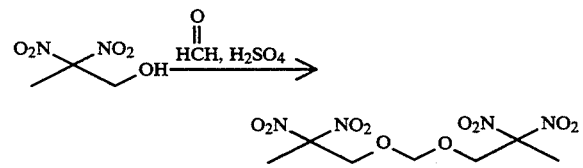

In the synthesis process, solid 2,2-dinitropropanol is mixed with a formaldehyde source to form a reaction solution. A slight stoichiometric excess of the formaldehyde source, such that more than one mole of formaldehyde is present for every two moles of DNPOH, is preferably used in the reaction. Examples of typical formaldehyde sources include s-trioxane and paraformaldehyde. The formaldehyde source generates formaldehyde in situ for participation in the reaction with 2,2-dinitropropanol.

A protic acid catalyst is then slowly added to the reaction solution. Protic acid catalysts are preferably selected from inorganic acids such as $H_2SO_4$, HCl, $H_3PO_4$, and HBr. During the addition, the reaction solution is preferably maintained at a temperature below 30° C. and agitated.

Upon completion of the reaction, the reaction solution is quenched with water. The water extracts the protic acid catalyst, water soluble reactants, and water soluble byproducts from the reaction solution. The reaction solution is then washed with an inorganic base solution, such as a hydroxide solution. Sufficient hydroxide is used to neutralize the protic acid catalyst and to solubilize unreacted 2,2-dinitropropanol as the nitronate salt, as well as any other aqueous soluble byproducts in the reaction solution. During the hydroxide wash, the pH is preferably kept sufficiently low to prevent hydrolysis of the BDNPF product. It is currently preferred to maintain the pH below 14 and preferably below 11.

A low boiling temperature polar organic solvent which does not contain chlorine is added to extract the BDNPF product. Methyl tert-butyl ether (MTBE) is the currently preferred polar organic solvent. Although other low boiling temperature polar organic solvent may be used to extract BDNPF, it has been found that MTBE is able to extract BDNPF at sufficiently high purity such that the BDNPF product is usable for military applications without further purification, such as recrystallization or high temperature vacuum distillation. The exposure time and concentration of the inorganic base solution is preferably limited to prevent hydrolysis of the polar organic solvent.

The aqueous phase is removed and discarded. The organic phase is washed with water. Finally, the organic solvent is evaporated to yield usable BDNPF product. The resulting yield is at least 60%, and preferably at least 70%, based on the starting quantity of 2,2-dinitropropanol. The evaporation is preferably accomplished at a temperature less than 60° C. and at a pressure less than about 150 mm Hg, and more preferably at a temperature less than 50° C. and at a pressure less than 20 mm Hg.

DETAILED DESCRIPTION OF THE INVENTION

The present invention is directed to a process of synthesizing bis(2,2-dinitropropyl)formal (BDNPF). In the process, 2,2-dinitropropanol (DNPOH) is reacted at low temperature with a formaldehyde source in the presence of a protic acid catalyst.

In the synthesis process, 2,2-dinitropropanol is mixed with a formaldehyde source to form a reaction solution. Typical formaldehyde sources include s-trioxane and paraformaldehyde. The formaldehyde source generates formaldehyde in situ for participation in the reaction with 2,2-dinitropropanol. The reaction is preferably carried out such that a slight stoichiometric excess of formaldehyde is produced by the formaldehyde source, that is, more than one mole of formaldehyde is present for every two moles of 2,2-dinitropropanol.

A protic acid catalyst is then slowly added to the reaction solution. The protic acid catalyst is preferably selected from include $H_2SO_4$, HCl, $H_3PO_4$, and HBr. The protic acid catalyst participates in the reaction as a catalyst or dehydrating agent instead of a combinatorial reagent. That is, the acid catalyst does not combine with the 2,2-dinitropropanol or formaldehyde source to form the final BDNPF product.

During the protic acid catalyst addition, the reaction solution is preferably agitated. To inhibit byproduct formation, the reaction temperature during the protic acid catalyst addition is preferably from about $-30°$ C. to $30°$ C., more preferably from about $-10°$ C. to $10°$ C., and most preferably from about $0°$ C. to $5°$ C. Although the BDNPF product is produced at higher temperatures, as the temperature increases, an increasing amount of undesirable byproducts are also produced. In addition, low temperatures are preferred to inhibit hydrolysis of the BDNPF product by the protic acid catalyst.

Upon completion of the reaction, the reaction solution is quenched with water. The water extracts the protic acid catalyst, water soluble reactants, and water soluble byproducts from the reaction solution.

The reaction solution is washed with an inorganic base solution, such as a hydroxide solution. The hydroxide concentration should be sufficient to neutralize the protic acid catalyst and to solubilize unreacted 2,2-dinitropropanol as the nitronate salt, as well as any other aqueous soluble byproducts in the reaction solution. The pH during the inorganic base wash is preferably kept sufficiently low to prevent hydrolysis of the BDNPF product. It is currently preferred to balance the amount of base solution used with its concentration such that the pH is maintained below about 11 during the initial base solution wash. The pH may be higher in a second base solution wash, but is preferably kept below 14. The hydroxide concentration may range from 1% to 25%, by weight. The hydroxide solution can be prepared from a number of different hydroxide salts known in the art, such as NaOH, KOH, and LiOH. A 5%, by weight, NaOH solution is currently preferred.

Finally, the BDNPF product is extracted with a polar organic solvent which does not contain chlorine. Suitable solvents should have a boiling temperature below 125° C., preferably below 100° C., and most preferably below about 80° C., at ambient pressure. The organic solvent preferably does not react with the inorganic base under the exposure time and concentration conditions used in the process. It has been found that methyl tert-butyl ether (MTBE) is able to extract BDNPA at sufficiently high purity such that the BDNPA product is usable for military applications without further purification.

The aqueous phase is removed and discarded. The organic phase is washed with pure water to remove any remaining water soluble byproducts or reactants. Finally, the organic solvent is evaporated to yield usable BDNPF product. The resulting yield is at least 60%, and preferably at least 70%, based on the starting quantity of 2,2-dinitropropanol. The evaporation is preferably accomplished at a temperature less than 60° C. and at a pressure less than about 150 mm Hg, and more preferably at a temperature less than 50° C. and at a pressure less than 20 mm Hg.

As used herein, usable BDNPF product includes BDNPF of sufficient purity that a 50:50 mixture of BDNPA/BDNPF meets military density, refractive index and acid aging standards. The military specification for a 50:50 BDNPA/BDNPF mixture requires that the density be between 1.38–1.40 g/cc, the refractive index be between 1.462 and 1.464, and the acid aging test be below 0.5 mg KOH/g nitroplasticizer. In the acid aging text, the BDNPF nitroplasticizer is aged in an oven at 105° C. for 7 days. After aging, the sample is titrated with KOH to determine the acid content. The result is reported as mg KOH/g nitroplasticizer.

The following examples are offered to further illustrate the present invention. These examples are intended to be purely exemplary and should not be viewed as a limitation on any claimed embodiment.

EXAMPLE 1

Bis(2,2-dinitropropyl)formal (BDNPF) was synthesized by mixing 3.95 g (26.3 mmole) 2,2-dinitropropanol (DNPOH) and 0.44 g (14.6 meq) s-trioxane in an empty, dry reaction vessel that had been purged with dry nitrogen. The DNPOH and s-trioxane reaction solution was cooled to $-8°$ C. 2 ml of $H_2SO_4$ were slowly added to the reaction solution while keeping the reaction solution temperature below 5° C. During the addition, the reaction solution was stirred and maintained under nitrogen atmosphere. After addition of the $H_2SO_4$, the mixture went from liquid to solid. A NMR analysis of the product showed 23 mole % DNPOH, 4.6 mole % diformal, and 72 mole % BDNPF.

The mixture was allowed to warm up to room temperature which resulted in a slurry of solid and liquid material. A NaOH solution was prepared by dissolving 2.9 g NaOH in 80 ml water, i.e., sufficient hydroxide to neutralize the $H_2SO_4$. The reaction products and the NaOH solution were cooled to 0° C., and the NaOH solution was added to the reaction products.

The solid BDNPF was extracted with 3×30 ml of MTBE (methyl tert-butyl ether). The MTBE solutions were combined and washed with 3×10 ml of 5%, by weight, NaOH solution followed by 3×10 ml $H_{20}$ washings. The aqueous phases were discarded and the organic phase dried with $MgSO_4$. The MTBE was evaporated at 20° C. and less than 20 mm Hg, leaving 3.11 g (76% yield) usable BDNPF.

EXAMPLE 2

Bis(2,2-dinitropropyl)formal is synthesized according to the procedure of Example 1 except that the protic acid catalyst is HCl instead of $H_2SO_4$. In this example, 2 ml of concentrated hydrochloric acid are used.

EXAMPLE 3

Bis (2,2-dinitropropyl)formal is synthesized according to the procedure of Example 1 except that the paraformaldehyde (14.6 meq) is used as the formaldehyde source instead of s-trioxane.

EXAMPLE 4

Bis(2,2-dinitropropyl)formal (BDNPF) is synthesized according to the procedure of Example 1, except that the 2,2-dinitropropanol and the s-trioxane are mixed in a reaction vessel containing 4 ml hexane. The hexane helps solubilize the solid BDNPF product and does not participate in the reaction. The hexane also helps distribute heat and maintain temperature control. The hexane is removed from the final BDNPF product during evaporation of the polar organic solvent, MTBE.

EXAMPLE 5

Bis(2,2-dinitropropyl)formal (BDNPF), synthesized according to the scaled-up procedure of Example 1 without further purification, was mixed with BDNPA in a 50:50 weight ratio. The BDNPA/BDNPF mixture was tested to determine its purity according to military specifications. The mixture's density was found to be 1.38 g/cc, within the military specification range of 1.38 to 1.40 g/cc. The mixture's refractive index was measured to be 1.4635, within the military specification range of 1.462 to 1.464. Finally, the mixture was subjected to the acid aging test and had a result of 0.36 g KOH/g BDNPA, below the military specification upper limit of 0.5 g KOH/g BDNPA.

From the foregoing, it will be appreciated that the present invention provides a method for synthesizing BDNPF which does not use chlorinated solvents and which avoids costly and dangerous distillation procedures.

The present invention may be embodied in other specific forms without departing from its essential characteristics. The described embodiments are to be considered in all respects only as illustrative and not restrictive. The scope of the invention is, therefore, indicated by the appended claims rather than by the foregoing description.

The claimed invention is:

1. A process of synthesizing bis(2,2-dinitropropyl)formal (BDNPF) comprising the steps of:
   (a) mixing 2,2-dinitropropanol with a stoichiometric excess of a formaldehyde source to form a reaction solution;
   (b) adding a protic acid catalyst to the reaction solution, wherein said protic acid catalyst participates in the process as a catalyst or dehydration agent and not as a combinatorial reagent, wherein the reaction solution is maintained at a temperature in the range from about −30° C. to 30° C. during said adding step and wherein the reaction solution is agitated during said adding step;
   (c) washing the reaction solution with an aqueous hydroxide solution having a hydroxide ion concentration sufficient to neutralize the protic acid catalyst and to solubilize unreacted 2,2-dinitropropanol;
   (d) extracting BDNPF product with methyl tert-butyl ether (MTBE); and
   (e) evaporating the organic solvent to yield usable BDNPF product without further purification, wherein the resulting yield is at least 60% based on the starting quantity of 2,2-dinitropropanol, said evaporating step occurring at a temperature less than 60° C. and at a pressure of less than 150 mm Hg.

2. A process of synthesizing BDNPF as defined in claim 1, wherein the reaction solution is maintained at a temperature in the range from about −10° C. to 10° C. during protic acid catalyst addition.

3. A process of synthesizing BDNPF as defined in claim 1, wherein the reaction solution is maintained at a temperature in the range from about −5° C. to 5° C. during protic acid catalyst addition.

4. A process of synthesizing BDNPF as defined in claim 1, wherein the formaldehyde source is selected from s-trioxane and paraformaldehyde.

5. A process of synthesizing BDNPF as defined in claim 1, wherein the aqueous hydroxide solution has a hydroxide concentration in the range from 1% to 25%, by weight.

6. A process of synthesizing BDNPF as defined in claim 1, wherein aqueous hydroxide solution is prepared from a hydroxide salt selected from NaOH, KOH, and LiOH.

7. A process of synthesizing BDNPF as defined in claim 1, wherein the protic acid catalyst is selected from $H_2SO_4$, HCl, $H_3PO_4$, and HBr.

8. A process of synthesizing BDNPF as defined in claim 1, wherein the evaporating step occurs at a temperature less than 50° C. and at a pressure of less than 20 mm Hg.

9. A process of synthesizing BDNPF as defined in claim 1, wherein the 2,2-dinitropropanol and formaldehyde source reaction solution is further mixed with an immiscible organic solvent which does not contain chlorine.

10. A process of synthesizing BDNPF as defined in claim 1, wherein the yield of BDNPF product is at least 70% based on the starting quantity of 2,2-dinitropropanol.

11. A process of synthesizing bis(2,2-dinitropropyl)formal (BDNPF) comprising the steps of:
    (a) mixing 2,2-dinitropropanol with a formaldehyde source to form a reaction solution, wherein the formaldehyde source is selected from s-trioxane and paraformaldehyde, and wherein a stoichiometric excess of formaldehyde source is mixed with 2,2-dinitropropanol, wherein the reaction solution consists essentially of the 2,2-dinitropropanol and formaldehyde source mixture;
    (b) adding a protic acid catalyst selected from $H_2SO_4$, HCl, $H_3PO_4$, and HBr to the reaction solution, wherein said protic acid catalyst participates in the process as a catalyst or dehydration agent and not as a combinatorial reagent, wherein the reaction solution is maintained at a temperature in the range from about −30° C. to 30° C. during said adding step, and wherein the reaction solution is agitated during said adding step;
    (c) quenching the reaction solution with water to facilitate removal of soluble reactants and by-products from the reaction solution;
    (d) washing the reaction solution with an aqueous hydroxide solution prepared from a hydroxide salt selected from NaOH, KOH, and LiOH, wherein said aqueous hydroxide solution has a hydroxide concentration in the range from 1% to 25%, by weight, and wherein said sufficient hydroxide solution is added to the reaction solution to neutralize the protic acid catalyst and to solubilize unreacted 2,2-dinitropropanol and other aqueous soluble by-products in the reaction solution;
    (e) extracting BDNPF product with methyl tert-butyl ether (MTBE);
    (f) rinsing the BDNPF product with pure water to remove any remaining soluble reactants or by-products; and
    (g) evaporating the organic solvent to yield usable BDNPF product without further purification, wherein the resulting yield is at least 60% based on the starting quantity of 2,2-dinitropropanol, said evaporating step occurring at a temperature less than 60° C. and at a pressure of less than 150 mm Hg.

12. A process of synthesizing BDNPF as defined in claim 11, wherein the reaction solution is maintained at a temperature in the range from about −10° C. to 10° C. during protic acid catalyst addition.

13. A process of synthesizing BDNPF as defined in claim 11, wherein the reaction solution is maintained at a temperature in the range from about −5° C. to 5° C. during protic acid catalyst addition.

14. A process of synthesizing BDNPF as defined in claim 11, wherein the 2,2-dinitropropanol and formaldehyde source reaction solution is further mixed with an immiscible organic solvent which does not contain chlorine.

15. A process of synthesizing BDNPF as defined in claim 11, wherein the yield of BDNPF product is at least 70% based on the starting quantity of 2,2-dinitropropanol.

* * * * *